(12) United States Patent
Gulsun et al.

(10) Patent No.: US 12,094,112 B2
(45) Date of Patent: Sep. 17, 2024

(54) CORONARY LUMEN AND REFERENCE WALL SEGMENTATION FOR AUTOMATIC ASSESSMENT OF CORONARY ARTERY DISEASE

(71) Applicant: SIEMENS HEALTHINEERS AG, Forccheim (DE)

(72) Inventors: Mehmet Akif Gulsun, Princeton, NJ (US); Puneet Sharma, Princeton Junction, NJ (US); Diana Ioana Stoian, Brasov (RO); Max Schöbinger, Hirschaid (DE)

(73) Assignee: Siemens Healthineers AG, Forchheim (DE)

( * ) Notice: Subject to any disclaimer, the term of this patent is extended or adjusted under 35 U.S.C. 154(b) by 361 days.

(21) Appl. No.: 17/649,067

(22) Filed: Jan. 27, 2022

(65) Prior Publication Data

US 2023/0237648 A1    Jul. 27, 2023

(51) Int. Cl.
| | | |
|---|---|---|
| G06T 7/00 | (2017.01) |
| G06T 7/10 | (2017.01) |
| G16H 30/40 | (2018.01) |
| G16H 50/20 | (2018.01) |
| A61B 6/00 | (2006.01) |
| A61B 6/50 | (2024.01) |

(52) U.S. Cl.
CPC .............. *G06T 7/0012* (2013.01); *G06T 7/10* (2017.01); *G16H 30/40* (2018.01); *G16H 50/20* (2018.01); *A61B 6/504* (2013.01); *A61B 6/5217* (2013.01); *G06T 2207/20081* (2013.01); *G06T 2207/30048* (2013.01); *G06T 2207/30096* (2013.01); *G06T 2207/30101* (2013.01)

(58) Field of Classification Search
CPC .......... G06T 7/00; G06T 7/10; G06T 7/0012; G06T 2207/30101; G06T 2207/30096; G06T 2207/30048; G06T 2207/20081; A61B 6/504; G16H 30/40; G16H 50/20
See application file for complete search history.

(56) References Cited

U.S. PATENT DOCUMENTS 9,697,603 B2 *   7/2017   Reynolds .................. G06T 5/92
10,872,698 B2 * 12/2020   Itu .......................... G16H 50/50

FOREIGN PATENT DOCUMENTS

CN    110852987 A       2/2020
EP       3786972   *   8/2019   ............. G16H 30/20

OTHER PUBLICATIONS

U.S. Appl. No. 17/249,651, filed Mar. 9, 2021, entitled "Multi-Task Learning Framework for Fully Automated Assessment of Coronary Artery Disease," 40 pgs.

(Continued)

*Primary Examiner* — Tuan H Nguyen

(57) ABSTRACT

Systems and methods for automated assessment of a vessel are provided. One or more input medical images of a vessel of a patient are received. A plurality of vessel assessment tasks for assessing the vessel is performed using a machine learning based model trained using multi-task learning. The plurality of vessel assessment tasks comprises segmentation of reference walls of the vessel from the one or more input medical images and segmentation of lumen of the vessel from the one or more input medical images. Results of the plurality of vessel assessment tasks are output.

23 Claims, 9 Drawing Sheets

(56) References Cited

OTHER PUBLICATIONS

Extended European Search Report (EESR) mailed Jun. 26, 2023 in corresponding European Patent Application No. 23153098.1.
Kim Sekeun et al: "Fully Automatic Segmentation of Coronary Arteries Based on Deep Neural Network in Intravascular Ultrasound Images", Oct. 17, 2018 (Oct. 17, 2018), SAT 2015 18th International Conference, Austin, TX, USA, Sep. 24-27, 2015; [Lecture Notes in Computer Science; Lect.Notes Computer], Springer, Berlin, Heidelberg, pp. 161-168.
Li Jianning et al: "Multi-Task Deep Convolutional Neural Network for the Segmentation of Type B Aortic Dissection", arxiv.org, Cornell University Library, 201 Olin Library Cornell University Ithaca, NY 14853, Jun. 26, 2018 (Jun. 26, 2018).

* cited by examiner

CORONARY LUMEN AND REFERENCE WALL SEGMENTATION FOR AUTOMATIC ASSESSMENT OF CORONARY ARTERY DISEASE

TECHNICAL FIELD

The present invention relates generally to the automatic assessment of CAD coronary artery disease, and in particular to coronary lumen and reference wall segmentation for automatic assessment of coronary artery disease.

BACKGROUND

CAD (coronary artery disease) is characterized by the buildup of plaque in the coronary arteries, causing narrowing of the coronary arteries and a reduction of blood flow to the heart. The narrowing of the coronary arteries is referred to as a stenosis. The assessment of stenoses is performed based on coronary CTA (computed tomography angiography) imaging.

Various approaches have been proposed for the automatic assessment of stenoses. In one conventional approach, the diameter or area of the healthy coronary artery is estimated from coronary CTA imaging by either interpolating the diameter or area of the lumen between healthy ends of the coronary artery or by iteratively fitting a line to the diameter or area profile of the lumen. However, this conventional approach is unable to accurately assess stenoses when the plaque buildup is diffused and long or when the plaque buildup goes through a bifurcation in the coronary arteries. In another conventional approach, AI (artificial intelligence) based systems are trained to assess stenoses based on synthetically generated vessel trees. However, this conventional approach also suffers from the limitations of using only the diameter or area profile of the lumen, reducing its accuracy.

BRIEF SUMMARY OF THE INVENTION

In accordance with one or more embodiments, systems and methods for automated assessment of a vessel are provided. One or more input medical images of a vessel of a patient are received. A plurality of vessel assessment tasks for assessing the vessel is performed using a machine learning based model trained using multi-task learning based on shared features extracted from the one or more input medical images. The plurality of vessel assessment tasks comprises segmentation of reference walls of the vessel from the one or more input medical images and segmentation of lumen of the vessel from the one or more input medical images. Results of the plurality of vessel assessment tasks are output.

In one embodiment, the machine learning based model is trained for the segmentation of the reference wall of the vessel based on regularization for anatomical tapering of the vessel.

In one embodiment, the machine learning based model is trained for the segmentation of the reference wall of the vessel and the segmentation of the lumen of the vessel based on regularization for consistency between results of the segmentation of the reference walls of the vessel and results of the segmentation of the lumen of the vessel in regions without anomalies or lesions. The regularization for consistency between the results of the segmentation of the reference walls of the vessel and the results of the segmentation of the lumen of the vessel in the regions without anomalies or lesions is based on ground truth markers for the anomalies and ground truth markers for the lesions.

In one embodiment, the machine learning based model is trained for the segmentation of the reference wall of the vessel based on regularization for the segmentation of the reference wall in regions with anomalies or lesions. The regularization for the segmentation of the reference wall in the regions with anomalies or lesions is based on ground truth markers for the anomalies and ground truth markers for the lesions.

In one embodiment, the machine learning based model is trained for the segmentation of the reference wall of the vessel and the segmentation of the lumen of the vessel based on regularization for consistency between ground truth stenosis grading and stenosis grading based on results of the segmentation of the reference walls of the vessel and results of the segmentation of the lumen.

In one embodiment, the machine learning based model is trained for the segmentation of the lumen of the vessel for consistency between ground truth lumen segmentation and results of the segmentation of the lumen.

In one embodiment, the plurality of vessel assessment tasks further comprises image-based stenosis grading of a stenosis in the vessel and wherein results of the image-based stenosis grading, results of the segmentation of the references walls, and results of the segmentation of the lumen are consistent.

In one embodiment, a stenosis grade of a stenosis in the vessel is determined based on the segmentation of the reference walls of the vessel and the segmentation of the lumen of the vessel.

In one embodiment, an uncertainty estimate for each of the plurality of vessel assessment tasks is determined.

These and other advantages of the invention will be apparent to those of ordinary skill in the art by reference to the following detailed description and the accompanying drawings.

DETAILED DESCRIPTION

The present invention generally relates to methods and systems for coronary lumen and reference wall segmentation for automatic assessment of CAD (coronary artery disease). Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for a multi-task learning framework for end-to-end training of a single machine learning based model for performing segmentation of a reference wall of a vessel and segmentation of lumen of the vessel, along with other vessel assessment tasks (e.g., stenosis grading) for the assessment of CAD. The joint determination of the segmentation of the reference wall and the segmentation of the lumen by the single machine learning based model provides accurate segmentation and stenosis grading results that are robust to image artifacts and poor image quality. By utilizing the single machine learning based model, results of each of the plurality of vessel assessment tasks are ensured to be consistent. In addition, the single end-to-end machine learning based model may produce meaningful results regardless of the failure of an individual medical imaging analysis task.

Figure 1:
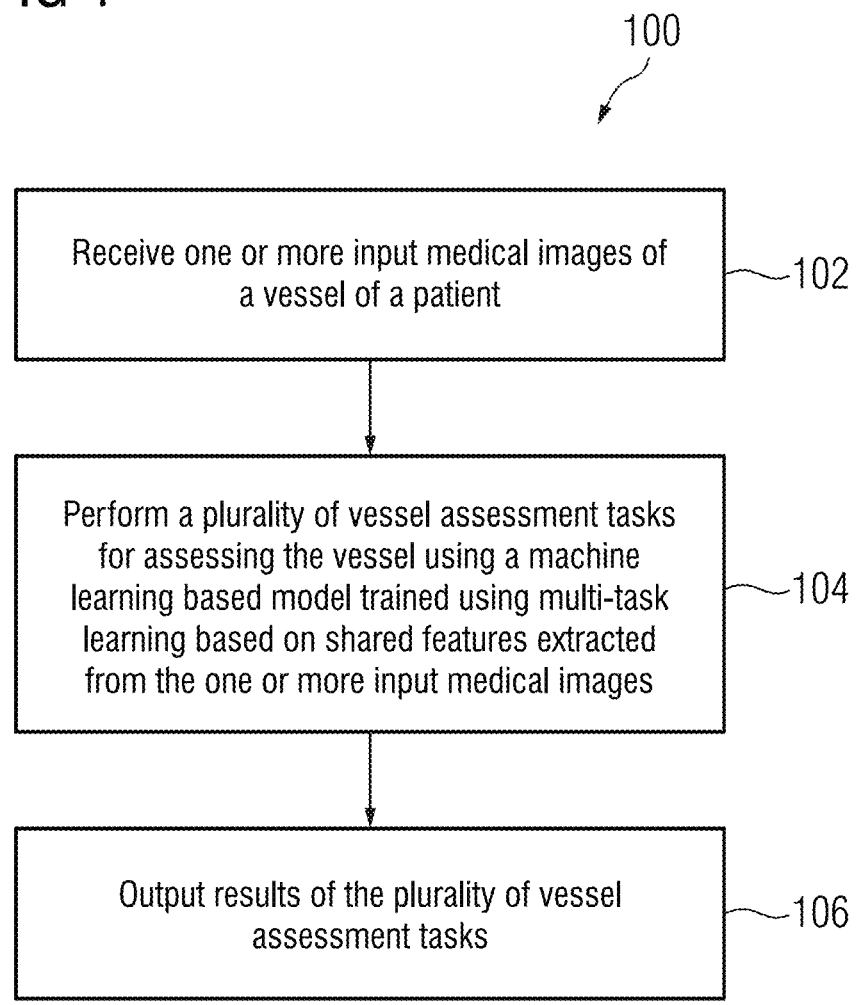
FIG. 1 shows a method for automatic assessment of a vessel, in accordance with one or more embodiments.

FIG. 1 shows a method 100 for automatic assessment of a vessel, in accordance with one or more embodiments. The steps of method 100 may be performed by one or more suitable computing devices, such as, e.g., computer 902 of FIG. 9.

At step 102 of FIG. 1, one or more input medical images of a vessel of a patient are received. The vessel of the patient may be an artery of the patient, a vein of the patient, or any other vessel of the patient. For example, the vessel may be a coronary branch of the patient, an intracranial or extracranial vessel of the patient, the aorta of the patient, peripheral vessels of the patient, etc. The input medical images may depict plaque or other abnormalities (e.g., lesions, nodules, or any other abnormality) on the walls of the vessel.

In one embodiment, the input medical images comprise cross-sectional images of the vessel sampled along the vessel. However, the input medical images may comprise any suitable images of the vessel and are not limited to cross-sectional images of the vessel. In some embodiments, the input medical images may include features such as, e.g., reformatted views of the vessel, geometric features of the vessel (e.g., distance to an anatomical landmark or other anatomical object of interest, estimates of the diameter of the vessel, etc.), anatomical features of the vessel (e.g., labels identifying the vessel, indicators of bifurcations in the vessel, etc.), or any other suitable features of the vessel.

In one embodiment, the input medical images are CT (computed tomography) images, such as, e.g., CTA (computed tomography angiography) images. Such CTA images may be single phase CTA images or multi-phase CTA images. However, the input medical images may be of any other suitable modality, such as, e.g., MRI (magnetic resonance imaging), x-ray, US (ultrasound), or any other modality or combination of modalities. The input medical images may comprise 2D (two dimensional) images or 3D (three dimensional) volumes, and may comprise a single image or a plurality of images (e.g., a sequence of images acquired over time). The input medical images may be received directly from an image acquisition device (e.g., image acquisition device 914 of FIG. 9), such as, e.g., a CT scanner, as the images are acquired, or can be received by loading previously acquired images from a storage or memory of a computer system or receiving images from a remote computer system.

At step 104 of FIG. 1, a plurality of vessel assessment tasks for assessing the vessel is performed using a machine learning based model trained using multi-task learning based on shared features extracted from the one or more input medical images. The plurality of vessel assessment tasks may be any suitable task for assessing the vessel.

In one embodiment, the plurality of vessel assessment tasks includes segmentation of reference walls of the vessel. As used herein, the reference walls of the vessel refer to the walls of the vessel when healthy, excluding any disease or abnormalities (e.g., plaque, lesions, nodules, or any other abnormality) on the walls of the vessel. Various metrics may be calculated based on the segmented reference walls of the vessel, such as, e.g., the diameter (e.g., effective diameter or minimum/maximum diameter) or area of the reference walls of the vessel.

In one embodiment, the plurality of vessel assessment tasks includes segmentation of lumen of the vessel. Various metrics may be calculated based on the segmented lumen of the vessel, such as, e.g., the diameter (e.g., effective diameter or minimum/maximum diameter) or area of the lumen of the vessel.

In one embodiment, the plurality of vessel assessment tasks includes image-based stenosis grading of a stenosis in the vessel. As used herein, image-based stenosis grading refers to stenosis grading performed directly from the shared features without using results of a segmentation of the lumen of the vessel. The stenosis may be graded or classified as being, e.g., normal, minimal, mild, moderate, severe, or occluded, or may be graded as percent stenosis.

The plurality of vessel assessment tasks may comprise any other vessel assessment task, such as, e.g., detection and classification of a disease (e.g., coronary artery disease), detection and classification of artifacts in the input medical images, detection and classification of anomalies in the input medical images, detection and classification of anomalies (e.g., myocardial bridging, or anomalies due to prior interventions (e.g., stents, bypass grafts, etc.)), and image-based determination of hemodynamic indices (e.g., FFR (fractional flow reserve), CFR (coronary flow reserve), iFR (instantaneous wave-free ratio), etc.) for the vessel.

In one embodiment, the machine learning based model comprises 1) an encoder for encoding the one or more input medical images into the shared features (i.e., latent features or a latent representation) and 2) a plurality of decoders each for decoding the shared features to perform a respective one of the plurality of vessel assessment tasks. The machine learning based model may be any suitable machine learning based model or models for performing the plurality of vessel assessment tasks, such as, e.g., a DNN (deep neural network), a CNN (convolutional neural network), a DI2IN (deep image-to-image network), etc. In one embodiment, the machine learning based model is implemented according to framework 200 of FIG. 2 or framework 600 of FIG. 6, described in detail below. The machine learning based model is trained to perform the plurality of vessel assessment tasks using multi-task learning during a prior offline or training stage based on annotated training data. In one embodiment, the machine learning based model may be trained in accordance with framework 500 of FIG. 5, described in detail below. Once trained, the trained machine learning based model is applied (e.g., at step 104) to perform the plurality of vessel assessment tasks during an online or testing stage.

Figure 2:
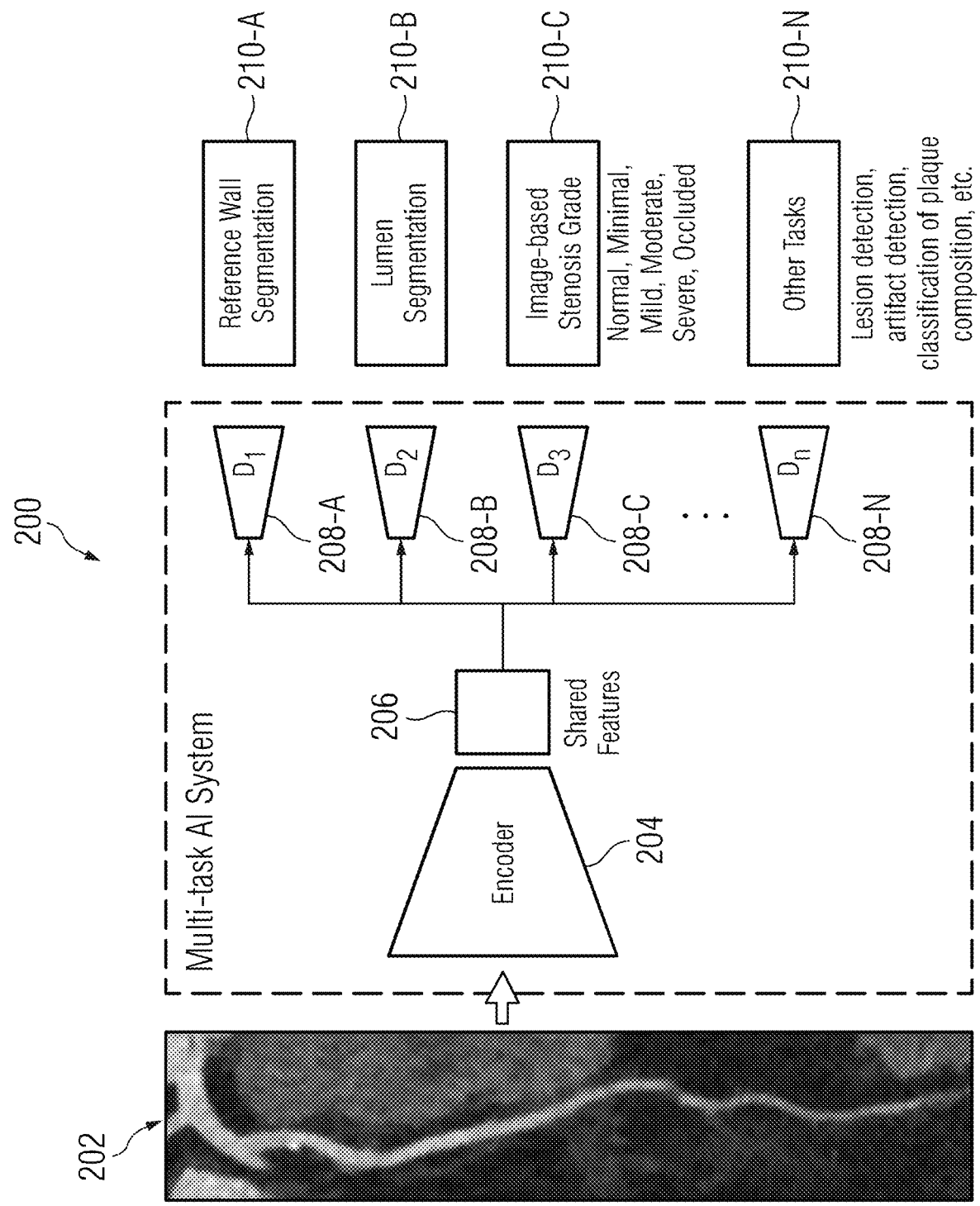
FIG. 2 shows a multi-task learning framework of a machine learning based model trained using multi-task learning to perform a plurality of vessel assessment tasks, in accordance with one or more embodiments.

FIG. 2 shows a multi-task learning framework 200 of a machine learning based model trained using multi-task learning to perform a plurality of vessel assessment tasks, in accordance with one or more embodiments. Framework 200 may be the framework of the machine learning based model applied at step 104 of FIG. 1. In framework 200, encoder 204 of the machine learning based model receives as input one or more input medical images 202 of a vessel of a patient and encodes the one or more input medical images 202 into shared features 206. Encoder 204 may be a VAE (variational autoencoder). Decoders D1 208-A, D2 208-B, D3 208-C, and Dn 208-N (collectively referred to as a plurality of decoders 208) of the machine learning based model decode shared features 206 to perform a respective vessel assessment task 210-A, 210-B, 210-C, 210-D, and 210-N (collectively referred to as a plurality of vessel assessment tasks 210). As shown in framework 200, vessel assessment task 210-A is for reference wall segmentation, vessel assessment task 210-B is for lumen segmentation, vessel assessment task 210-C is for image-based stenosis grading (e.g., as being normal, minimal, mild, moderate, severe, or occluded), and vessel assessment task 210-N is for other vessel assessment tasks, such as, e.g., lesion detection, artifact detection, classification of plaque composition, etc. As the plurality of vessel assessment tasks 210 are jointly performed by a single machine learning based model from shared features 206, results of each of the plurality of vessel assessment tasks 210 are ensured to be consistent. Additionally, the machine learning based model can produce meaningful results regardless of the failure in an individual task.

At step 106 of FIG. 1, results of the plurality of vessel assessment tasks are output. For example, the results of the plurality of vessel assessment tasks can be output by displaying the results of the plurality of vessel assessment tasks on a display device of a computer system, storing the results of the plurality of vessel assessment tasks on a memory or storage of a computer system, or by transmitting the results of the plurality of vessel assessment tasks to a remote computer system.

In one embodiment, the results of the plurality of vessel assessment tasks may be output to other systems. In one embodiment, the results of the plurality of vessel assessment tasks may be output to fully automated coronary analysis systems or to fully automated FFR (fractional flow reserve) prediction systems. Such FFR prediction systems would be robust to image quality issues (e.g., artificial narrowing of segmentation results around imaging artifacts). In another embodiment, the results of the plurality of vessel assessment tasks may be output to an outer wall segmentation algorithm as a soft or hard regularization constraint to improve results around difficult lesions (e.g., non-calcified plaque).

In one embodiment, results of the segmentation of the reference wall of the vessel and results of the segmentation of the lumen of the vessel may be presented overlaid over the input medical images.

In one embodiment, a stenosis grade of a stenosis in the vessel may be determined based on the segmentation of the reference walls and the segmentation of the lumen of the vessel.

Figure 3:
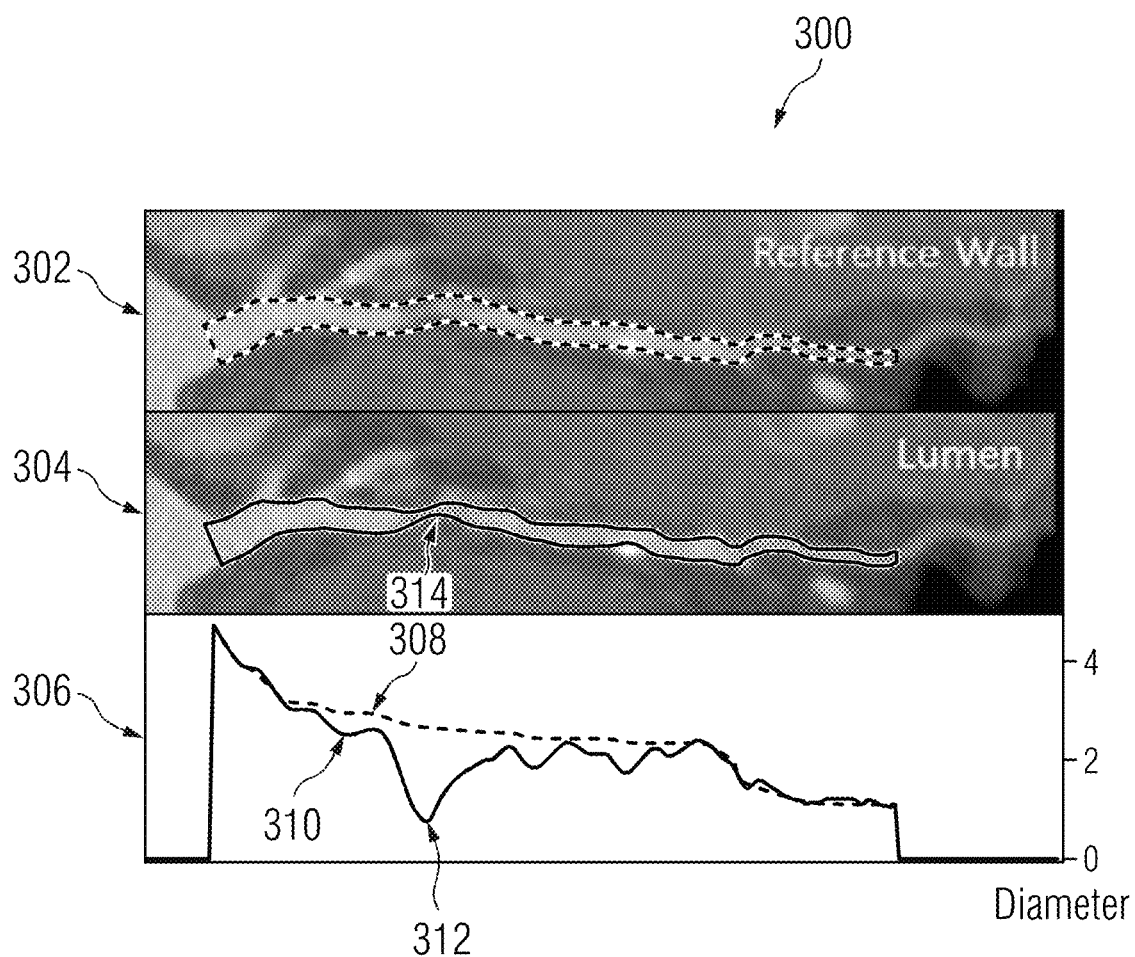
FIG. 3 shows results of vessel assessment tasks for segmentation of a reference wall of a vessel and for segmentation of lumen of the vessel generated in accordance with one or more embodiments.

FIG. 3 shows results 300 of vessel assessment tasks for segmentation of a reference wall of a vessel and for segmentation of lumen of the vessel generated in accordance with one or more embodiments. Image 302 shows a segmentation of the reference wall of the vessel overlaid on an MPR (multiplanar reformation) image and image 304 shows a segmentation of the lumen of the vessel overlaid on the MPR image. The segmentation of the reference wall and the segmentation of the lumen may be respective results of vessel assessment tasks 210-A and 210-B of FIG. 2. Graph 306 compares the effective diameter of the reference wall (line 308) with the effective diameter of the lumen (line 310). As shown in graph 306, the diameter of the lumen of the vessel significantly deviates from the diameter of reference wall of the vessel at point 312, indicating a stenosis 314 shown in the results of the segmentation of the lumen in image 304.

Figure 4:
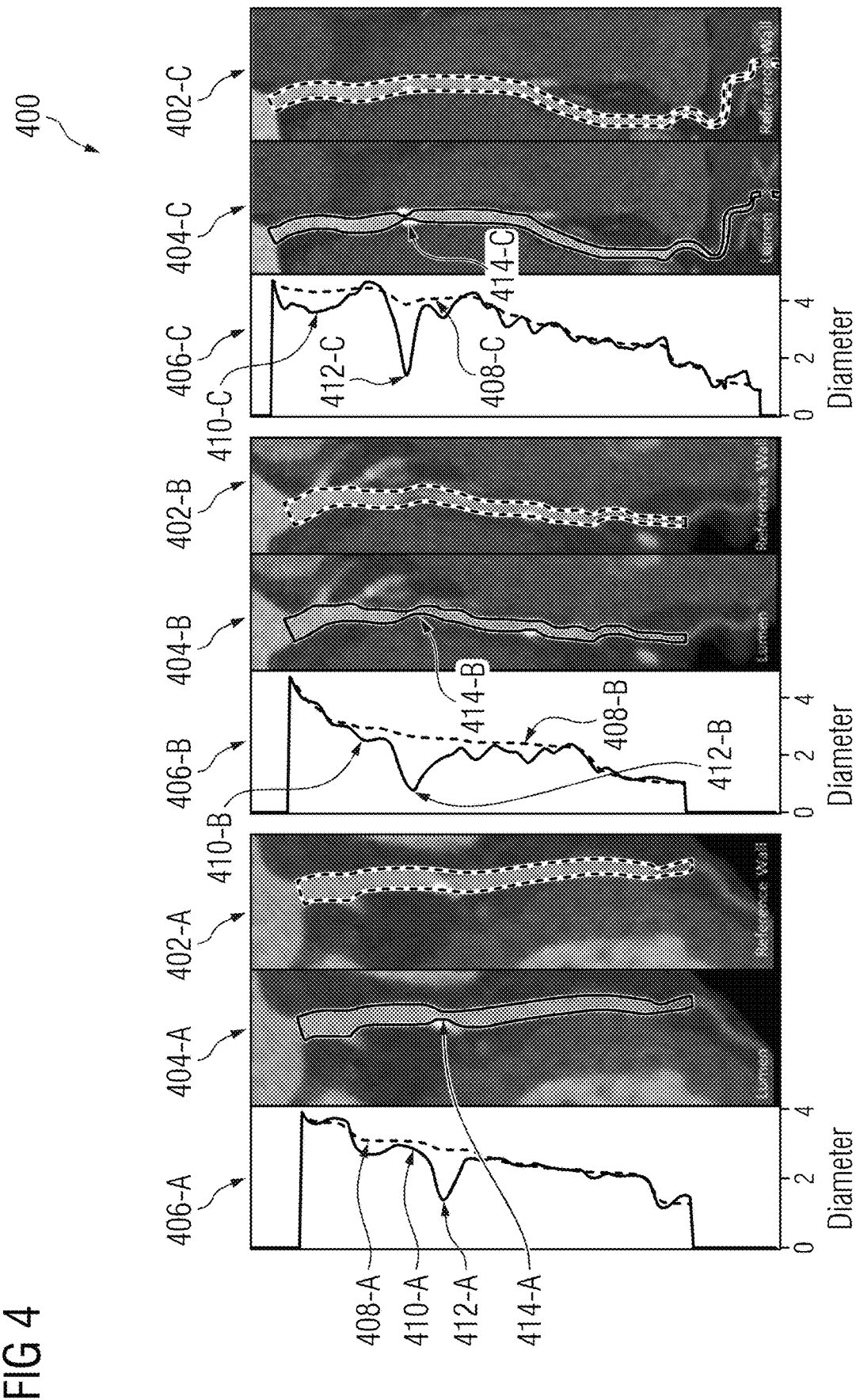
FIG. 4 shows results of vessel assessment tasks for segmentations of reference walls of vessels and results of segmentations of lumen of the vessels from various input medical images, in accordance with one or more embodiments.

FIG. 4 shows results 400 of vessel assessment tasks for segmentations of reference walls of vessels and results of segmentations of lumen of the vessels from various input medical images, in accordance with one or more embodiments. The segmentations of the reference walls and the segmentations of the lumen may be respective results of vessel assessment tasks 210-A and 210-B of FIG. 2. Images 402-A, 402-B, and 402-C show segmentations of reference walls of respective vessels overlaid over MPR images. Images 404-A, 404-B, and 404-C show segmentations of lumen of the respective vessels overlaid over the MPR images. Graphs 406-A, 406-B, and 406-C compare the effective diameter of the reference walls (lines 408-A, 408-B, and 408-C) with the effective diameter of the lumen (410-A, 410-B, and 410-C). As shown in graph 406-A, the diameter of the lumen of the vessel significantly deviates from the diameter of reference wall of the vessel at point 412-A, indicating a stenosis 414-A shown in the results of the segmentation of the lumen in image 404-A. As shown in graph 406-B, the diameter of the lumen of the vessel significantly deviates from the diameter of reference wall of the vessel at point 412-B, indicating a stenosis 414-B shown in the results of the segmentation of the lumen in image 404-B. As shown in graph 406-C, the diameter of the lumen of the vessel significantly deviates from the diameter of reference wall of the vessel at point 412-C, indicating a stenosis 414-C shown in the results of the segmentation of the lumen in image 404-C.

Advantageously, embodiments described herein enable fully automated assessment of coronary artery disease while producing explainable results of vessel assessment tasks with localization of findings. Embodiments described herein jointly perform segmentation of reference walls of the vessel and segmentation of lumen of the vessel, thereby increasing accuracy and robustness to image artifacts and poor image quality. Further, embodiments described herein jointly train a single end-to-end machine learning based model for performing a plurality of vessel assessment tasks. This ensures consistency of the results between different vessel assessment tasks, as well as improved performance and generalization by sharing features between related vessel assessment tasks. Embodiments described herein may be extended to coronary vessel analysis on invasively acquired 2D angiography images.

Figure 5:
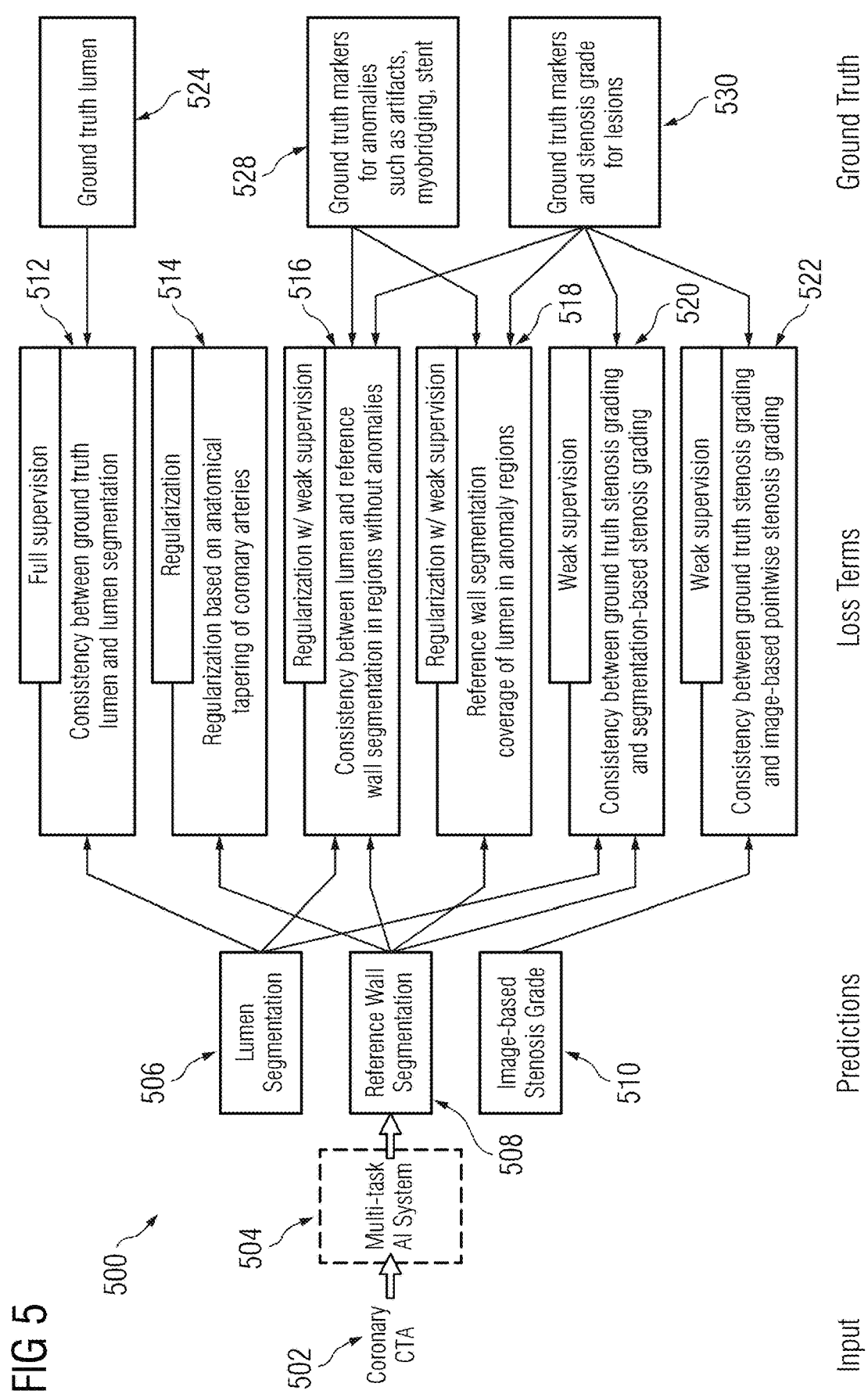
FIG. 5 shows a framework for training a multi-task AI (artificial intelligence) system for performing a plurality of vessel assessment tasks, in accordance with one or more embodiments.

FIG. 5 shows a framework 500 for training a multi-task AI (artificial intelligence) system 504 for performing a plurality of vessel assessment tasks, in accordance with one or more embodiments. In one embodiment, multi-task AI system 504 may be the machine learning based model applied at step 104 of FIG. 1, the machine learning based model shown in FIG. 2, or the machine learning based model shown in FIG. 6 (described below). Framework 500 trains the multi-task AI system 504 using multi-task learning to perform a plurality of vessel assessment tasks. As shown in framework 500, multi-task AI system 504 receives coronary CTA training images 502 as input and generates predictions a plurality of vessel assessment tasks comprising lumen segmentation 506, reference wall segmentation 508, and image-based stenosis grading 510. The predictions are used together with ground truth data for optimizing an objective function for training multi-task AI system 504. The objective function is computed as a weighted sum of different loss terms 512-522 with supervision, weak supervision, regularization, and/or regularization with weak supervision.

Multi-task AI system 504 is trained by optimizing an objective function comprising one or more of the following loss terms:

1) full supervision 512 to enforce consistency between ground truth lumen 524 and lumen segmentation;
2) regularization 514 to enforce regularization based on anatomical tapering of coronary arteries;
3) regularization with weak supervision 516 to enforce consistency between lumen and reference wall segmentation in regions without anomalies or lesions (using ground truth markers 528 for anomalies such as, e.g., artifacts, myo-bridging, and stents and ground truth markers and stenosis grades 530 for lesions such as, e.g., plaque);
4) regularization with weak supervision 518 to enforce reference wall segmentation coverage of lumen in anomaly or lesion regions (using ground truth markers 528 and ground truth markers and stenosis grades 530) to ensure the full coverage of lumen segmentation output inside reference wall segmentation output;
5) weak supervision 520 to enforce consistency between ground truth stenosis grading 530 and segmentation-based stenosis grading based on results of the segmentation of the reference walls of the vessel and results of the segmentation of the lumen of the vessel; and
6) weak supervision 522 to enforce consistency between ground truth stenosis grading 530 and image-based pointwise stenosis grading.

As shown in FIG. 5, multi-task AI system 504 is trained for lumen segmentation 506 using full supervision 512, regularization with weak supervision 516, and weak supervision 520. Multi-task AI system 504 is trained for reference wall segmentation 508 using regularization 514, regularization with weak supervision 516, regularization with weak supervision 518, and weak supervision 520. Multi-task AI system 504 is trained for image-based stenosis grading 510 using weak supervision 522. It is noted that multi-task AI system 504 is trained for reference wall segmentation 508 without using ground truth markers or annotations of the reference wall, as such ground truth markers are not available for vessels having plaque and other lesions on its walls. Exemplary loss functions could be, for example (but not limited to), dice or cross-entropy loss for full supervision 512, sum of the positive differences of consecutive terms of effective diameters derived from reference wall segmentation for regularization 514, dice or cross-entropy loss for regularization with weak supervision 516 and 518, cross-entropy classification loss for weak supervision 520, and L1/L2 loss for weak supervision 520.

In one embodiment, multi-task AI system 504 may be trained with ground truth FFR (fractional flow reserve) values measured invasively or calculated based on CT images (CT-FFR) for weakly supervised optimization to generate results of vessel assessment tasks (e.g., segmentation or image-based FFR calculation) that conform with each other. For example, multi-task AI system 504 may be trained to generate segmentation results that conform with image-based FFR predictions or invasive or CT-based FFR measurements.

In one embodiment, the machine learning based model applied at step 104 of FIG. 1 may determine a confidence measure for results of the plurality of vessel assessment tasks. The confidence measure may be a confidence measure for the plurality of vessel assessment tasks as a whole, which would indicate a level of consistency between the plurality of vessel assessment tasks. The confidence measure may also be a confidence measure determined for each of the results of the plurality of vessel assessment tasks. The confidence measure may be represented in any suitable form, such as, e.g., a confidence score, a heatmap representing the confidence, etc. In one example, a confidence measure is determined for the segmentation of the reference wall of the vessel and the segmentation of the lumen of the vessel. In one embodiment, the confidence measure may be determined by varying the threshold used for generating contours/meshes from segmentations. In another embodiment, the confidence measure may be determined as an uncertainty estimate that can be predicted in conjunction with the output segmentation probability. For example, the final layer of the machine learning based model can be replaced with a Gaussian process to output a probability distribution for uncertainty estimation, as shown in FIG. 6.

Figure 6:
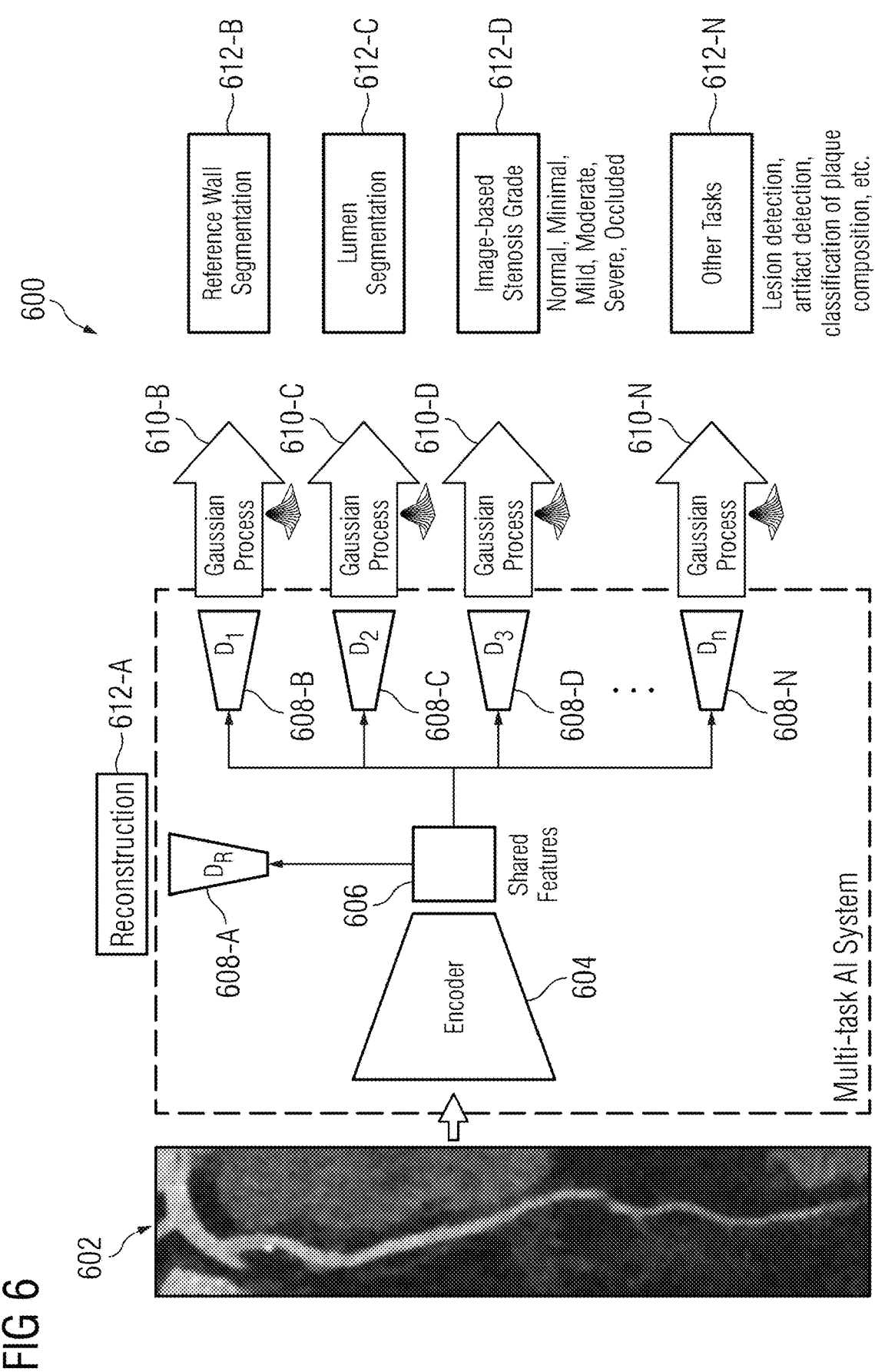
FIG. 6 shows a multi-task learning framework of a machine learning based model trained using multi-task learning to perform a plurality of vessel assessment tasks determined with uncertainty estimation, in accordance with one or more embodiments.

FIG. 6 shows a multi-task learning framework 600 of a machine learning based model trained using multi-task learning to perform a plurality of vessel assessment tasks determined with uncertainty estimation, in accordance with one or more embodiments. Framework 600 may be the framework of the machine learning based model applied at step 104 of FIG. 1. In framework 600, encoder 604 of the machine learning based model receives as input one or more input medical images 602 of a vessel of a patient and encodes the one or more input medical images 602 into shared features 606. Decoders Dr 608-A, D1 608-B, D2 608-C, D3 608-D, and Dn 608-N (collectively referred to as a plurality of decoders 608) of the machine learning based model decode shared features 606 to perform a respective vessel assessment task 612-A, 612-B, 612-C, 612-D, and 612-N (collectively referred to as a plurality of vessel assessment tasks 612). As shown in framework 600, vessel assessment task 612-A is for reconstruction of input medical image 602, vessel assessment task 612-B is for reference wall segmentation, vessel assessment task 612-C is for lumen segmentation, vessel assessment task 612-D is for image-based stenosis grading as being normal, minimal, mild, moderate, severe, or occluded, and vessel assessment task 612-N is for other vessel assessment tasks, such as, e.g., lesion detection, artifact detection, classification of plaque composition, etc. The final layer of decoders 608-B, 608-C, 608-D, and 608-N are replaced with a respective Gaussian process 610-B, 610-C, 610-D, and 610-N to output a probability distribution for uncertainty estimation. A Gaussian process is not applied for decoder 608-A for reconstruction task 612-A of input medical images 602. Reconstruction task 612-A regularizes the manifold for training to thereby regularize shared features 606.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, ( ) learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 7:
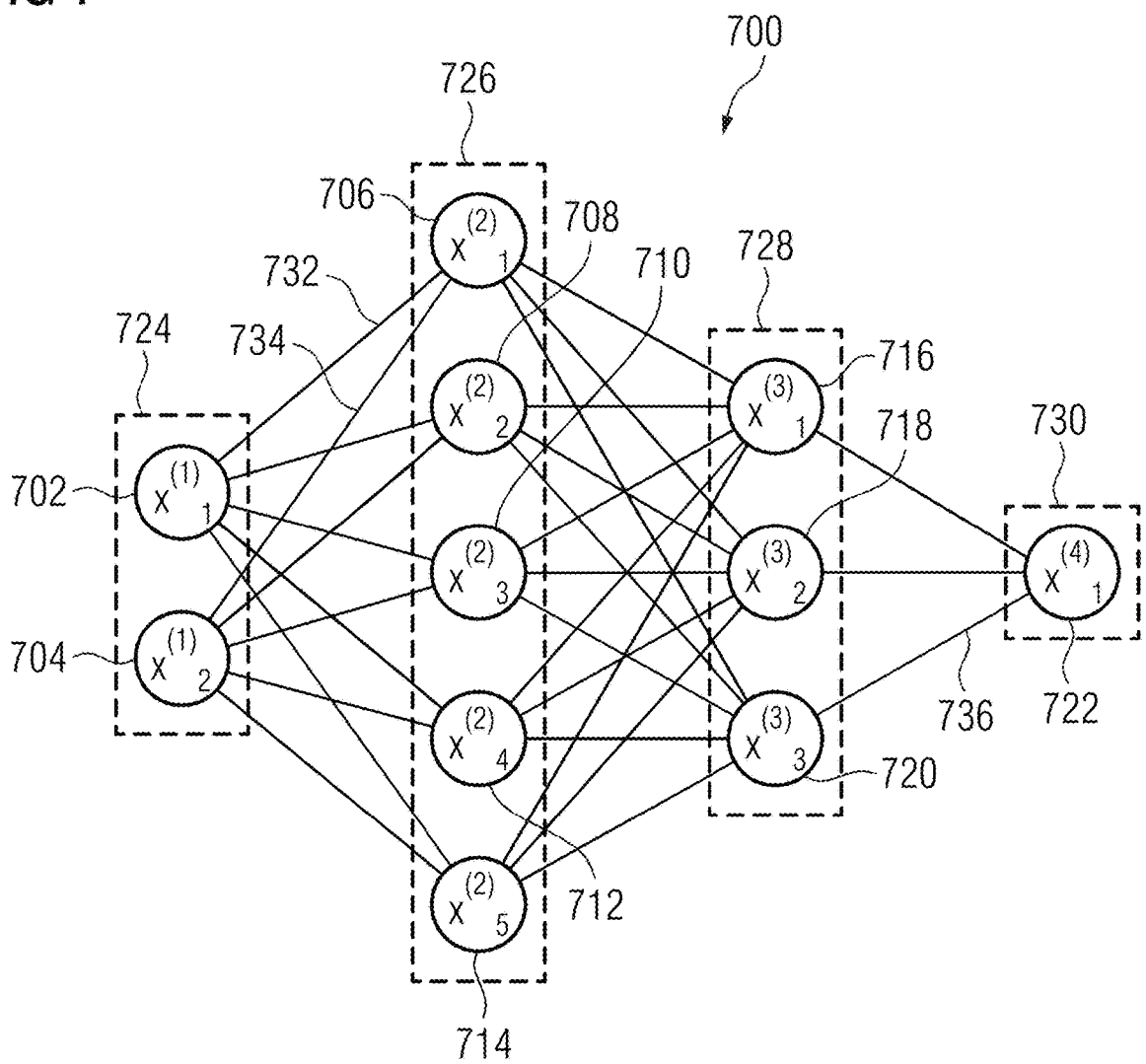
FIG. 7 shows an exemplary artificial neural network that may be used to implement one or more embodiments.

FIG. 7 shows an embodiment of an artificial neural network 700, in accordance with one or more embodiments. Alternative terms for "artificial neural network" are "neural network", "artificial neural net" or "neural net". Machine learning networks described herein, including the machine learning based model applied at step 104 of FIG. 1, encoder 204 and plurality of decoders 208 of FIG. 2, multi-task AI system 504 of FIG. 5, and encoder 604 and plurality of decoders 608 of FIG. 6, may be implemented using artificial neural network 700.

The artificial neural network 700 comprises nodes 702-722 and edges 732, 734, . . . , 736, wherein each edge 732, 734, . . . , 736 is a directed connection from a first node 702-722 to a second node 702-722. In general, the first node 702-722 and the second node 702-722 are different nodes 702-722, it is also possible that the first node 702-722 and the second node 702-722 are identical. For example, in FIG. 7, the edge 732 is a directed connection from the node 702 to the node 706, and the edge 734 is a directed connection from the node 704 to the node 706. An edge 732, 734, . . . , 736 from a first node 702-722 to a second node 702-722 is also denoted as "ingoing edge" for the second node 702-722 and as "outgoing edge" for the first node 702-722.

In this embodiment, the nodes 702-722 of the artificial neural network 700 can be arranged in layers 724-730, wherein the layers can comprise an intrinsic order introduced by the edges 732, 734, . . . , 736 between the nodes 702-722. In particular, edges 732, 734, . . . , 736 can exist only between neighboring layers of nodes. In the embodiment shown in FIG. 7, there is an input layer 724 comprising only nodes 702 and 704 without an incoming edge, an output layer 730 comprising only node 722 without outgoing edges, and hidden layers 726, 728 in-between the input layer 724 and the output layer 730. In general, the number of hidden layers 726, 728 can be chosen arbitrarily. The number of nodes 702 and 704 within the input layer 724 usually relates to the number of input values of the neural network 700, and the number of nodes 722 within the output layer 730 usually relates to the number of output values of the neural network 700.

In particular, a (real) number can be assigned as a value to every node 702-722 of the neural network 700. Here, $x^{(n)}_i$ denotes the value of the i-th node 702-722 of the n-th layer 724-730. The values of the nodes 702-722 of the input layer 724 are equivalent to the input values of the neural network 700, the value of the node 722 of the output layer 730 is equivalent to the output value of the neural network 700. Furthermore, each edge 732, 734, . . . , 736 can comprise a weight being a real number, in particular, the weight is a real number within the interval [−1, 1] or within the interval [0, 1]. Here, $wo^{(m,n)}_{i,j}$ denotes the weight of the edge between the i-th node 702-722 of the m-th layer 724-730 and the j-th node 702-722 of the n-th layer 724-730. Furthermore, the abbreviation $w^{(n)}_{i,j}$ is defined for the weight $w^{(n,n+1)}_{i,j}$.

In particular, to calculate the output values of the neural network 700, the input values are propagated through the neural network. In particular, the values of the nodes 702-722 of the (n+1)-th layer 724-730 can be calculated based on the values of the nodes 702-722 of the n-th layer 724-730 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions The transfer function is mainly used for normalization purposes.

In particular, the values are propagated layer-wise through the neural network, wherein values of the input layer 724 are given by the input of the neural network 700, wherein values of the first hidden layer 726 can be calculated based on the values of the input layer 724 of the neural network, wherein values of the second hidden layer 728 can be calculated based in the values of the first hidden layer 726, etc.

In order to set the values $w^{(m,n)}_{i,j}$ for the edges, the neural network 700 has to be trained using training data. In particular, training data comprises training input data and training output data (denoted as $t_i$). For a training step, the neural network 700 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 700 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein γ is a learning rate, and the numbers $\delta^{(n)}_j$ can be recursively calculated as $$\delta^{(n)}_j = (\Sigma_k \delta^{(n+1)}_k \cdot w^{(n+1)}_{j,k}) \cdot f'(\Sigma_i x^{(n)}_i \cdot w^{(n)}_{i,j})$$

based on $\delta^{(n+1)}_j$, if the (n+1)-th layer is not the output layer, and $$\delta^{(n)}_j = (x^{(n+1)}_k - t^{(n+1)}_j) \cdot f'(\Sigma_i x^{(n)}_i \cdot w^{(n)}_{i,j})$$

if the (n+1)-th layer is the output layer 730, wherein f' is the first derivative of the activation function, and $y^{(n+1)}_j$ is the comparison training value for the j-th node of the output layer 730.

Figure 8:
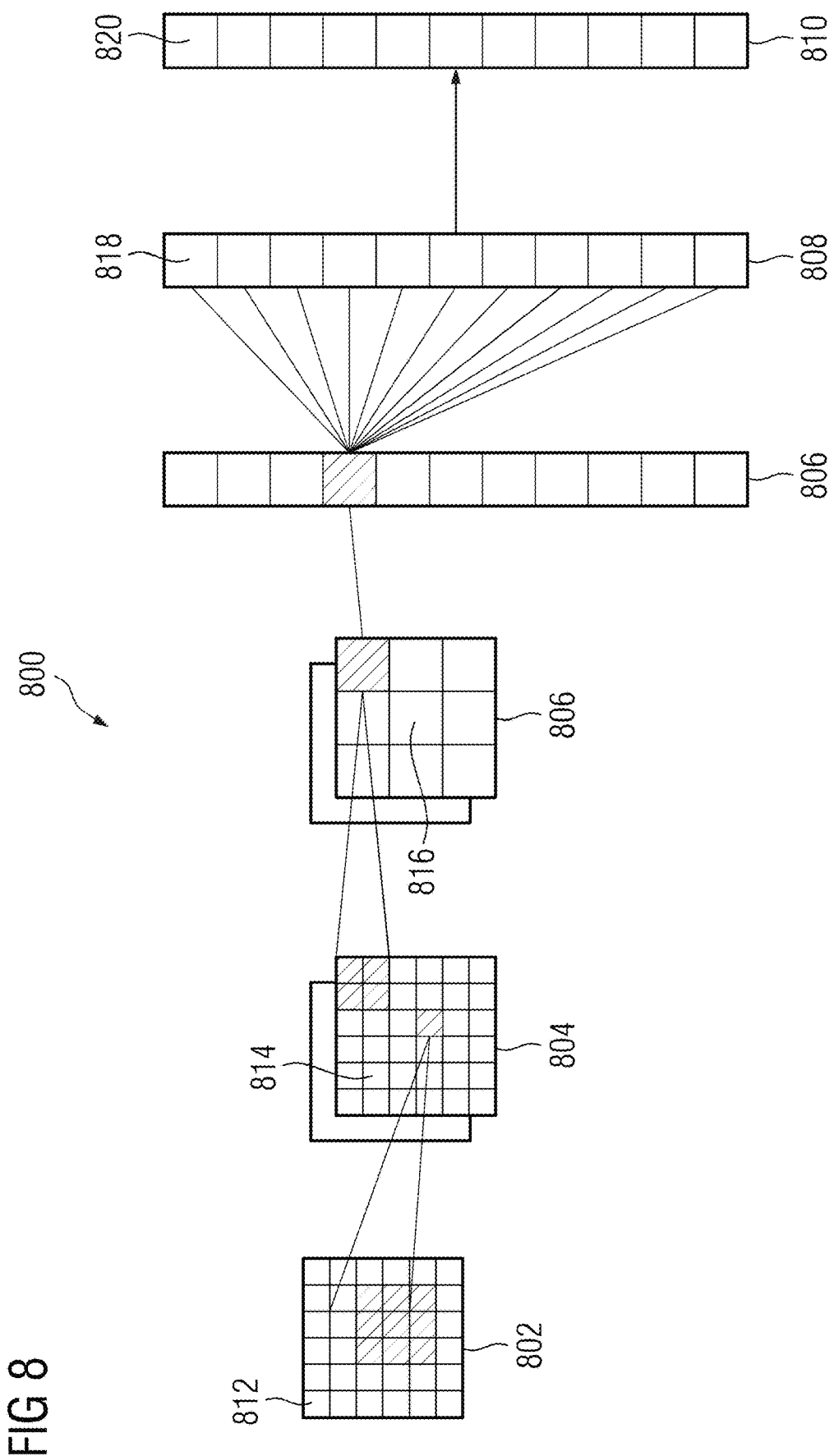
FIG. 8 shows a convolutional neural network that may be used to implement one or more embodiments.

FIG. 8 shows a convolutional neural network 800, in accordance with one or more embodiments. Machine learning networks described herein, including the machine learning based model applied at step 104 of FIG. 1, encoder 204 and plurality of decoders 208 of FIG. 2, multi-task AI system 504 of FIG. 5, and encoder 604 and plurality of decoders 608 of FIG. 6, may be implemented using convolutional neural network 800.

In the embodiment shown in FIG. 8, the convolutional neural network comprises 800 an input layer 802, a convolutional layer 804, a pooling layer 806, a fully connected layer 808, and an output layer 810. Alternatively, the convolutional neural network 800 can comprise several convolutional layers 804, several pooling layers 806, and several fully connected layers 808, as well as other types of layers. The order of the layers can be chosen arbitrarily, usually fully connected layers 808 are used as the last layers before the output layer 810.

In particular, within a convolutional neural network 800, the nodes 812-820 of one layer 802-810 can be considered to be arranged as a d-dimensional matrix or as a d-dimensional image. In particular, in the two-dimensional case the value of the node 812-820 indexed with i and j in the n-th layer 802-810 can be denoted as $x^{(n)}_{[i,j]}$. However, the arrangement of the nodes 812-820 of one layer 802-810 does not have an effect on the calculations executed within the convolutional neural network 800 as such, since these are given solely by the structure and the weights of the edges.

In particular, a convolutional layer 804 is characterized by the structure and the weights of the incoming edges forming a convolution operation based on a certain number of kernels. In particular, the structure and the weights of the incoming edges are chosen such that the values $x^{(n)}_k$ of the nodes 814 of the convolutional layer 804 are calculated as a convolution $x^{(n)}_k = K_k * x^{(n-1)}$ based on the values $x^{(n-1)}$ of the nodes 812 of the preceding layer 802, where the convolution * is defined in the two-dimensional case as $$x^{(n)}_k[i,j] = (K_k * x^{(n-1)})[i,j] = \Sigma_{i'} \Sigma_{j'} K_k[i',j'] \cdot x^{(n-1)}[i-i',j-j']$$

Here the k-th kernel $K_k$ is a d-dimensional matrix (in this embodiment a two-dimensional matrix), which is usually small compared to the number of nodes 812-818 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 812-820 in the respective layer 802-810. In particular, for a convolutional layer 804, the number of nodes 814 in the convolutional layer is equivalent to the number of nodes 812 in the preceding layer 802 multiplied with the number of kernels.

If the nodes 812 of the preceding layer 802 are arranged as a d-dimensional matrix, using a plurality of kernels can be interpreted as adding a further dimension (denoted as "depth" dimension), so that the nodes 814 of the convolutional layer 804 are arranged as a (d+1)-dimensional matrix. If the nodes 812 of the preceding layer 802 are already arranged as a (d+1)-dimensional matrix comprising a depth dimension, using a plurality of kernels can be interpreted as expanding along the depth dimension, so that the nodes 814 of the convolutional layer 804 are arranged also as a (d+1)-dimensional matrix, wherein the size of the (d+1)-dimensional matrix with respect to the depth dimension is by a factor of the number of kernels larger than in the preceding layer 802.

The advantage of using convolutional layers 804 is that spatially local correlation of the input data can exploited by enforcing a local connectivity pattern between nodes of adjacent layers, in particular by each node being connected to only a small region of the nodes of the preceding layer.

In embodiment shown in FIG. 8, the input layer 802 comprises 36 nodes 812, arranged as a two-dimensional 6×6 matrix. The convolutional layer 804 comprises 72 nodes 814, arranged as two two-dimensional 6×6 matrices, each of the two matrices being the result of a convolution of the values of the input layer with a kernel. Equivalently, the nodes 814 of the convolutional layer 804 can be interpreted as arranges as a three-dimensional 6×6×2 matrix, wherein the last dimension is the depth dimension.

A pooling layer 806 can be characterized by the structure and the weights of the incoming edges and the activation function of its nodes 816 forming a pooling operation based on a non-linear pooling function f. For example, in the two dimensional case the values x(n) of the nodes 816 of the pooling layer 806 can be calculated based on the values $x^{(n-1)}$ of the nodes 814 of the preceding layer 804 as $$x^{(n)}[i,j] = f(x^{(n-1)}[id_1, jd_2], \ldots, x^{(n-1)}[id_1+d_1-1, jd_2+d_2-1])$$

In other words, by using a pooling layer 806, the number of nodes 814, 816 can be reduced, by replacing a number d1-d2 of neighboring nodes 814 in the preceding layer 804 with a single node 816 being calculated as a function of the values of said number of neighboring nodes in the pooling layer. In particular, the pooling function f can be the max-function, the average or the L2-Norm. In particular, for a pooling layer 806 the weights of the incoming edges are fixed and are not modified by training.

The advantage of using a pooling layer 806 is that the number of nodes 814, 816 and the number of parameters is reduced. This leads to the amount of computation in the network being reduced and to a control of overfitting.

In the embodiment shown in FIG. 8, the pooling layer 806 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 808 can be characterized by the fact that a majority, in particular, all edges between nodes 816 of the previous layer 806 and the nodes 818 of the fully-connected layer 808 are present, and wherein the weight of each of the edges can be adjusted individually.

In this embodiment, the nodes 816 of the preceding layer 806 of the fully-connected layer 808 are displayed both as two-dimensional matrices, and additionally as non-related nodes (indicated as a line of nodes, wherein the number of nodes was reduced for a better presentability). In this embodiment, the number of nodes 818 in the fully connected layer 808 is equal to the number of nodes 816 in the preceding layer 806. Alternatively, the number of nodes 816, 818 can differ.

Furthermore, in this embodiment, the values of the nodes 820 of the output layer 810 are determined by applying the Softmax function onto the values of the nodes 818 of the preceding layer 808. By applying the Softmax function, the sum the values of all nodes 820 of the output layer 810 is 1, and all values of all nodes 820 of the output layer are real numbers between 0 and 1.

A convolutional neural network 800 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 800 can be trained based on the backpropagation algorithm. For preventing overfitting, methods of regularization can be used, e.g. dropout of nodes 812-820, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 9:
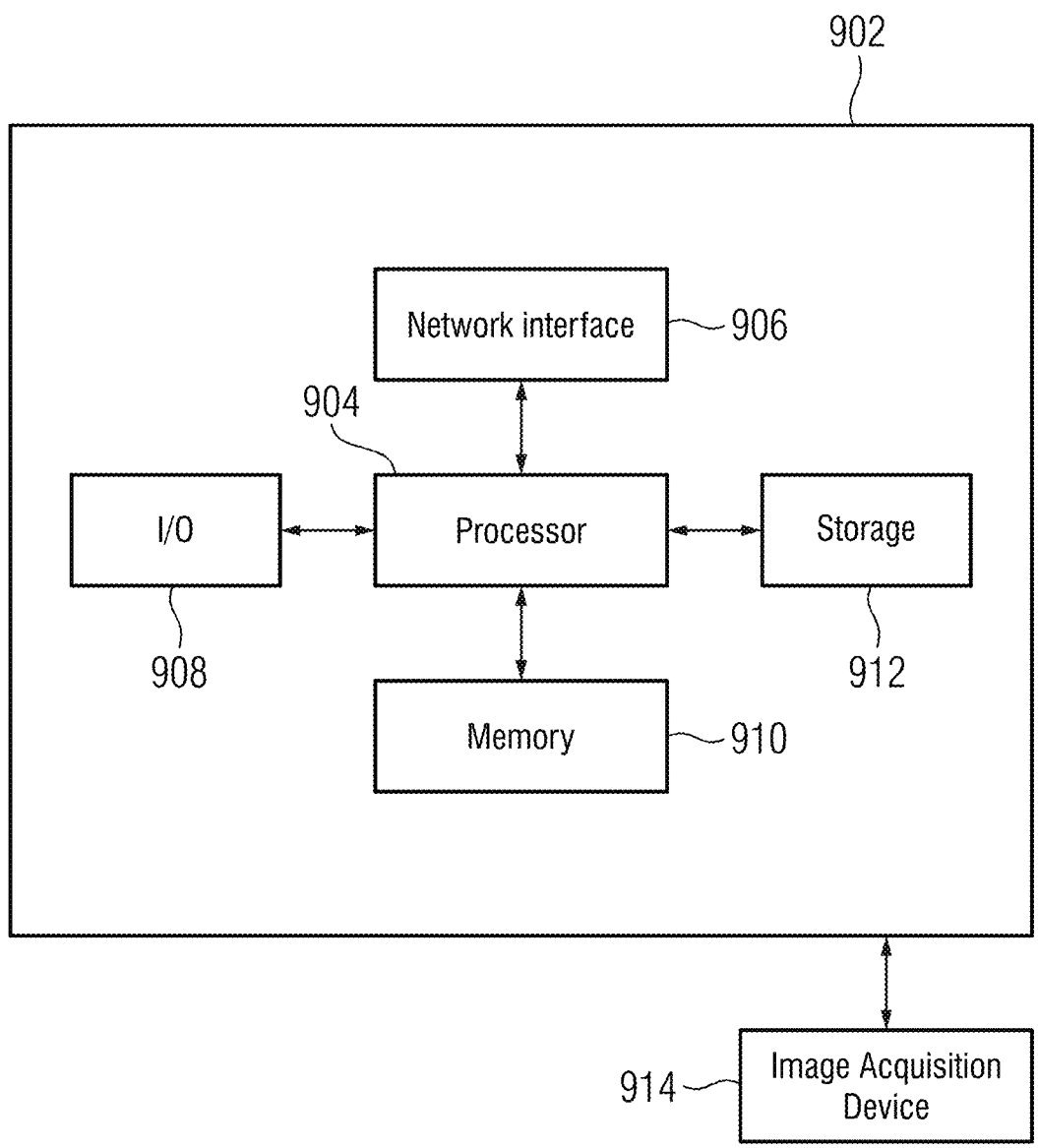
FIG. 9 shows a high-level block diagram of a computer that may be used to implement one or more embodiments.

A high-level block diagram of an example computer 902 that may be used to implement systems, apparatus, and methods described herein is depicted in FIG. 9. Computer 902 includes a processor 904 operatively coupled to a data storage device 912 and a memory 910. Processor 904 controls the overall operation of computer 902 by executing computer program instructions that define such operations. The computer program instructions may be stored in data storage device 912, or other computer readable medium, and loaded into memory 910 when execution of the computer program instructions is desired. Thus, the method and workflow steps or functions of FIG. 2 can be defined by the computer program instructions stored in memory 910 and/or data storage device 912 and controlled by processor 904 executing the computer program instructions. For example, the computer program instructions can be implemented as computer executable code programmed by one skilled in the art to perform the method and workflow steps or functions of FIG. 1. Accordingly, by executing the computer program instructions, the processor 904 executes the method and workflow steps or functions of FIG. 1. Computer 902 may also include one or more network interfaces 906 for communicating with other devices via a network. Computer 902 may also include one or more input/output devices 908 that enable user interaction with computer 902 (e.g., display, keyboard, mouse, speakers, buttons, etc.).

Processor 904 may include both general and special purpose microprocessors, and may be the sole processor or one of multiple processors of computer 902. Processor 904 may include one or more central processing units (CPUs), for example. Processor 904, data storage device 912, and/or memory 910 may include, be supplemented by, or incorporated in, one or more application-specific integrated circuits (ASICs) and/or one or more field programmable gate arrays (FPGAs).

Data storage device 912 and memory 910 each include a tangible non-transitory computer readable storage medium. Data storage device 912, and memory 910, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 908 may include peripherals, such as a printer, scanner, display screen, etc. For example, input/output devices 908 may include a display device such as a cathode ray tube (CRT) or liquid crystal display (LCD) monitor for displaying information to the user, a keyboard, and a pointing device such as a mouse or a trackball by which the user can provide input to computer 902.

An image acquisition device 914 can be connected to the computer 902 to input image data (e.g., medical images) to the computer 902. It is possible to implement the image acquisition device 914 and the computer 902 as one device. It is also possible that the image acquisition device 914 and the computer 902 communicate wirelessly through a network. In a possible embodiment, the computer 902 can be located remotely with respect to the image acquisition device 914.

Any or all of the systems and apparatus discussed herein may be implemented using one or more computers such as computer 902.

One skilled in the art will recognize that an implementation of an actual computer or computer system may have other structures and may contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
   receiving one or more input medical images of a vessel of a patient;
   performing a plurality of vessel assessment tasks for assessing the vessel using a machine learning based model trained using multi-task learning based on shared features extracted from the one or more input medical images, the plurality of vessel assessment tasks comprising segmentation of reference walls of the vessel from the one or more input medical images and segmentation of lumen of the vessel from the one or more input medical images, wherein the machine learning based model is trained for the segmentation of the reference wall of the vessel and the segmentation of the lumen of the vessel based on regularization for consistency between results of the segmentation of the reference walls of the vessel and results of the segmentation of the lumen of the vessel in regions without anomalies or lesions; and
   outputting results of the plurality of vessel assessment tasks.

2. The computer-implemented method of claim 1, wherein the machine learning based model is trained for the segmentation of the reference wall of the vessel based on regularization for anatomical tapering of the vessel.

3. The computer-implemented method of claim 1, wherein the regularization for consistency between the results of the segmentation of the reference walls of the vessel and the results of the segmentation of the lumen of the vessel in the regions without anomalies or lesions is based on ground truth markers for the anomalies and ground truth markers for the lesions.

4. The computer-implemented method of claim 1, wherein the machine learning based model is trained for the segmentation of the reference wall of the vessel based on regularization for the segmentation of the reference wall in regions with anomalies or lesions.

5. The computer-implemented method of claim 4, wherein the regularization for the segmentation of the reference wall in the regions with anomalies or lesions is based on ground truth markers for the anomalies and ground truth markers for the lesions.

6. The computer-implemented method of claim 1, wherein the machine learning based model is trained for the segmentation of the reference wall of the vessel and the segmentation of the lumen of the vessel based on regularization for consistency between ground truth stenosis grading and stenosis grading based on results of the segmentation of the reference walls of the vessel and results of the segmentation of the lumen.

7. The computer-implemented method of claim 1, wherein the machine learning based model is trained for the segmentation of the lumen of the vessel for consistency between ground truth lumen segmentation and results of the segmentation of the lumen.

8. The computer-implemented method of claim 1, wherein the plurality of vessel assessment tasks further comprises image-based stenosis grading of a stenosis in the vessel and wherein results of the image-based stenosis grading, results of the segmentation of the references walls, and results of the segmentation of the lumen are consistent.

9. The computer-implemented method of claim 1, further comprising:
determining a stenosis grade of a stenosis in the vessel based on the segmentation of the reference walls of the vessel and the segmentation of the lumen of the vessel.

10. The computer-implemented method of claim 1, wherein performing a plurality of vessel assessment tasks for assessing the vessel using a machine learning based model trained using multi-task learning based on shared features extracted from the one or more input medical images comprises:
determining an uncertainty estimate for each of the plurality of vessel assessment tasks.

11. An apparatus comprising:
means for receiving one or more input medical images of a vessel of a patient;
means for performing a plurality of vessel assessment tasks for assessing the vessel using a machine learning based model trained using multi-task learning based on shared features extracted from the one or more input medical images, the plurality of vessel assessment tasks comprising segmentation of reference walls of the vessel from the one or more input medical images and segmentation of lumen of the vessel from the one or more input medical images, wherein the machine learning based model is trained for the segmentation of the reference wall of the vessel and the segmentation of the lumen of the vessel based on regularization for consistency between results of the segmentation of the reference walls of the vessel and results of the segmentation of the lumen of the vessel in regions without anomalies or lesions; and
means for outputting results of the plurality of vessel assessment tasks.

12. The apparatus of claim 11, wherein the machine learning based model is trained for the segmentation of the reference wall of the vessel based on regularization for anatomical tapering of the vessel.

13. The apparatus of claim 11, wherein the regularization for consistency between the results of the segmentation of the reference walls of the vessel and the results of the segmentation of the lumen of the vessel in the regions without anomalies or lesions is based on ground truth markers for the anomalies and ground truth markers for the lesions.

14. The apparatus of claim 11, wherein the machine learning based model is trained for the segmentation of the reference wall of the vessel based on regularization for the segmentation of the reference wall in regions with anomalies or lesions.

15. The apparatus of claim 14, wherein the regularization for the segmentation of the reference wall in the regions with anomalies or lesions is based on ground truth markers for the anomalies and ground truth markers for the lesions.

16. The apparatus of claim 11, wherein the machine learning based model is trained for the segmentation of the reference wall of the vessel and the segmentation of the lumen of the vessel based on regularization for consistency between ground truth stenosis grading and stenosis grading based on results of the segmentation of the reference walls of the vessel and results of the segmentation of the lumen.

17. A non-transitory computer readable medium storing computer program instructions, the computer program instructions when executed by a processor cause the processor to perform operations comprising:
receiving one or more input medical images of a vessel of a patient;
performing a plurality of vessel assessment tasks for assessing the vessel using a machine learning based model trained using multi-task learning based on shared features extracted from the one or more input medical images, the plurality of vessel assessment tasks comprising segmentation of reference walls of the vessel from the one or more input medical images and segmentation of lumen of the vessel from the one or more input medical images, wherein the machine learning based model is trained for the segmentation of the reference wall of the vessel and the segmentation of the lumen of the vessel based on regularization for consistency between results of the segmentation of the reference walls of the vessel and results of the segmentation of the lumen of the vessel in regions without anomalies or lesions; and
outputting results of the plurality of vessel assessment tasks.

18. The non-transitory computer readable medium of claim 17, wherein the machine learning based model is trained for the segmentation of the reference wall of the vessel and the segmentation of the lumen of the vessel based on regularization for consistency between ground truth stenosis grading and stenosis grading based on results of the segmentation of the reference walls of the vessel and results of the segmentation of the lumen.

19. The non-transitory computer readable medium of claim 17, wherein the machine learning based model is trained for the segmentation of the lumen of the vessel for consistency between ground truth lumen segmentation and results of the segmentation of the lumen.

20. The non-transitory computer readable medium of claim 17, wherein the plurality of vessel assessment tasks further comprises image-based stenosis grading of a stenosis in the vessel and wherein results of the image-based stenosis grading, results of the segmentation of the references walls, and results of the segmentation of the lumen are consistent.

21. The non-transitory computer readable medium of claim 17, the operations further comprising:
determining a stenosis grade of a stenosis in the vessel based on the segmentation of the reference walls of the vessel and the segmentation of the lumen of the vessel.

22. The non-transitory computer readable medium of claim 17, wherein performing a plurality of vessel assessment tasks for assessing the vessel using a machine learning based model trained using multi-task learning based on shared features extracted from the one or more input medical images comprises:
determining an uncertainty estimate for each of the plurality of vessel assessment tasks.

23. The non-transitory computer readable medium of claim 17, wherein the regularization for consistency between the results of the segmentation of the reference walls of the vessel and the results of the segmentation of the lumen of the vessel in the regions without anomalies or lesions is based on ground truth markers for the anomalies and ground truth markers for the lesions.

* * * * *